(12) United States Patent
Jaafar et al.

(10) Patent No.: US 6,699,230 B2
(45) Date of Patent: Mar. 2, 2004

(54) APPARATUS AND METHOD FOR OUT-OF-HOSPITAL THROMBOLYTIC THERAPY

(75) Inventors: Ali Jaafar, Eden Prairie, MN (US); Victor I. Chornenky, Minnetonka, MN (US)

(73) Assignee: Minnesota Medical Physics, LLC, Eden Prairie, MN (US)

( * ) Notice: Subject to any disclaimer, the term of this patent is extended or adjusted under 35 U.S.C. 154(b) by 0 days.

(21) Appl. No.: 09/849,051

(22) Filed: May 7, 2001

(65) Prior Publication Data

US 2002/0045856 A1 Apr. 18, 2002

Related U.S. Application Data

(60) Provisional application No. 60/202,542, filed on May 10, 2000.

(51) Int. Cl.⁷ .............................................. A61M 31/00
(52) U.S. Cl. ...................................................... 604/508
(58) Field of Search ................................. 604/508, 151, 604/131

(56) References Cited

U.S. PATENT DOCUMENTS

| | | | | |
|---|---|---|---|---|
| 4,178,368 A | * | 12/1979 | Heimburger et al. | 424/94 |
| 4,741,736 A | * | 5/1988 | Brown | 604/134 |
| 4,850,972 A | * | 7/1989 | Schulman et al. | 604/151 |
| 4,950,245 A | * | 8/1990 | Brown et al. | 604/153 |
| 5,116,316 A | * | 5/1992 | Sertic et al. | 604/83 |
| 5,207,642 A | * | 5/1993 | Orkin et al. | 604/65 |
| 5,248,300 A | * | 9/1993 | Bryant et al. | 604/134 |
| 5,256,157 A | * | 10/1993 | Samiotes et al. | 604/246 |
| 5,389,078 A | * | 2/1995 | Zalesky et al. | 604/151 |
| 5,399,166 A | * | 3/1995 | Laing | 604/146 |
| 5,542,935 A | * | 8/1996 | Unger et al. | 604/190 |
| 5,573,506 A | * | 11/1996 | Vasko | 604/65 |
| 5,681,285 A | * | 10/1997 | Ford et al. | 604/151 |
| 5,807,336 A | * | 9/1998 | Russo et al. | 604/131 |
| 5,885,245 A | * | 3/1999 | Lynch et al. | 604/67 |
| 5,895,371 A | * | 4/1999 | Levitas et al. | 604/49 |
| 5,925,016 A | * | 7/1999 | Chornenky et al. | 604/96.01 |
| 6,053,887 A | * | 4/2000 | Levitas et al. | 604/49 |
| 6,070,761 A | * | 6/2000 | Bloom et al. | 222/81 |
| 6,074,366 A | * | 6/2000 | Rogers et al. | 604/151 |
| 6,230,501 B1 | * | 5/2001 | Bailey, Sr. et al. | 62/51.1 |
| 6,231,560 B1 | * | 5/2001 | Bui et al. | 604/500 |

* cited by examiner

Primary Examiner—Kevin Shaver
Assistant Examiner—Anuradha Ramana

(57) ABSTRACT

This invention provides an apparatus and method for emergency administration or self-administration of thrombolytic therapy in early stage of a heart attack. The apparatus includes a needle injector for making a venipuncture, a battery operated micro cooler for maintaining low temperature environment for vials with lyophilized thrombolytic and adjuvant drugs, a container with a diluent for reconstitution of the lyophilized drugs, a programmable infusion pump, and a microprocessor for controlling the process of infusion and recording the data. As the system is activated, said container becomes fluidly communicable with the infusion pump and vials with drugs in the cooler. Designed for autonomous execution of several schedules of infusion, it also can be controlled remotely by a qualified operator via an Internet interface.

1 Claim, 1 Drawing Sheet

APPARATUS AND METHOD FOR OUT-OF-HOSPITAL THROMBOLYTIC THERAPY

This application claims the benefit of 60/202,542 filed on May 10, 2000.

FIELD OF THE INVENTION

This invention relates to medical devices and more particularly to devices and methods for thrombolytic therapy of coronary arteries for patients experiencing an early stage of acute myocardial infarction.

BACKGROUND OF THE INVENTION

Acute myocardial infarction is a major cause of mortality and morbidity in an atherosclerosis-prone contemporary society. Each year approximately 1.5 million Americans suffer a myocardial infarction, and more than 400,000 individuals will likely die from it this year. Few life threatening diseases are as common as acute myocardial infarction. Myocardial infarction is the morphologic manifestation of irreversible cell death in an area of the heart that is caused by a prolonged, and often abrupt, mismatch between the supply of the oxygen and nutrients in the blood and the metabolic needs of the myocardial cells. The most common cause of this condition is the sudden interruption of blood flow in a coronary artery by an occlusive thrombus formed in an area with atherosclerotic disease. A myocardial infarction is an evolving, dynamic event. A coronary occlusion results in ischemia that is initially reversible, but over time becomes irreversible. Necrosis of myocardium, or cardiac muscle, begins 20 to 30 minutes after total occlusion of the vessel. This "wave front of necrosis" proceeds through the ischemic part of the myocardium and is complete within 4–6 hours of occlusion. Later a scar is formed over the necrotic part of the myocardium. The area of myocardium affected by infarction does not contribute any more to the overall pumping function of the heart.

To successfully salvage the myocardium, the blood flow though the occluded artery must be restored before the myocardium cells have been irreversibly destroyed. Restoration of the blood flow, or reperfusion, is more successful at the early stage of evolving infarction. Prompt therapy can make the difference between heart muscle death or salvage.

The most common method of reperfusion heart muscle during a myocardial infarction is the use of medications that dissolve thrombi-thrombolytic agents. Thrombolytic agents, including streptokinase, urokinase, anisteplase, and tissue plasminogen activator (tPA) are extremely efficient in preventing disability and the death among people having heart attacks. About 80 percent of people having a heart attack who receive a thrombolytic agent within 2 hours of the onset of symptoms have reperfusion. Successful reperfusion reduces the size of the myocardial infarction and helps preserve the overall pumping function of the heart.

There are several compelling reasons to start the thrombolytic therapy as early as possible. Probably, the best time for it is approximately 20–30 minutes after onset of symptoms, when no irreversible damage to the myocardium has been done yet. At this time the polymerization of fibrin in thrombus is still in progress and the thrombus is soft and easier to dissolve. This is because at this stage it is more permeable for the thrombolytic agents. The major mechanism of thrombolysis of totally occlusive thrombi is dragging the blood plasma with a thrombolytic agent in it through the body of thrombus by the blood pressure differential before and after the thrombus. Thus, early started thrombolytic therapy allows facilitates the faster dissolution of the thrombus. It is important also that for lysis of a very fresh thrombus that all thrombolytic agents are equally efficient. The tPA agent is about 10 times more expensive than streptokinase, but there is no difference in the time of dissolving of fresh thrombi.

Thus, very early thrombolytic therapy promises a complete salvage of the myocardium with the preservation of the overall pumping function of the heart, and it can be performed with a cost effective choice of thrombolytic drug. Mortality and morbidity of the patients suffering a myocardial infarction can be drastically reduced.

Whether or not thrombolytic treatment is undertaken or successful, additional treatment is usually required. Nitroglycerin is given either under the tongue or by vein to reduce symptoms by decreasing the heart's demand for oxygen and by improving the blood flow through coronary arteries as much as possible. Heart attacks can be very painful, so narcotics such as morphine are given when necessary. Medications such as beta-adrenergic blocking agents may be helpful for reducing pain and enhancing survival. Beta-adrenergic blockers make the heart beat more slowly and less forcefully, so it requires less oxygen. Blood clots can re-form in the coronary artery at the sites where thrombolysis has already dissolved the original blood clot. Thrombolytic drugs dissolve blood clots that already formed; anticoagulants prevent new blood clots from developing. A similar function is performed by antiplatelet medication like aspirin, which can be administered orally or intravenously.

Both thrombolytic therapy and supportive care are available in emergency rooms in hospitals. A lot of effort has been spent to provide the treatment as soon as possible. Nevertheless, the shortest time that passes before the treatment starts is still about two hours. At this time some damage to the myocardium is already done, and the treatment strategy is to minimize it and relieve the symptoms associated with this damage.

In many countries a special emergency mobile care paramedic unit has been introduced for cardiac patients with suspected myocardial infarction. With this "out-of-hospital" approach thrombolytic therapy can be delivered faster than in hospital emergency rooms. It is very promising way of improving cardiac care. The drawback of this approach is that the diagnosis and overall management of the patients by paramedics is not of the quality provided by highly qualified physicians in the emergency rooms in hospitals.

It is desirable that the emergency care be selected, prescribed and managed by the patient's personal cardiologist, who is familiar with the patient's cardiac history and general state of health.

It is desirable also to develop a method to provide a multiple medication therapy for cardiac patients suffering from a heart attack in its earliest stage, in the first 20–30 minutes after the onset of the symptoms. Such an early start would make real a new treatment strategy, the fundamental objective of which is the complete salvage of the myocardium and the preservation of 100% of its pumping function, rather than reducing to minimum the damage made in the first 2 hours.

There have been many known devices and methods for intravenous infusion of drugs, particularly drugs in a dry form, or lyophilized drugs, ready for reconstitution to liquid state before the usage. As an example, U.S. Pat. No. 5,024,657, assigned to Baxter International, and many others in U.S. class 604/85. This device is intended for hospital use by a qualified nurse or physician. It is not automated and can't be used by a person with little or no medical training.

It should be mentioned that a great number of contemporary drugs loose their activity within months of storage at room temperature. It is especially true for the protein based drugs, including thrombolytic agents. The system in accordance with the referred patent does not have a cooler and thus does not warrant the long-term efficiency of the drugs. It can not be held in a stand by state for a long period of time.

Another example of prior art can be U.S. Pat. No. 5,609,572, issued to Volker Lang. In this patent a modular cassette infusion system for multiple infusions and automatic administration of medicaments is described. For infusion control the system utilizes a microprocessor, which has fixed program and manual programming steps and is compatible with the infusion equipment. It substantially reduces the work to be performed by nursing staff. The device described in this patent requires manual reconstitution of dry drugs and does not allow keeping the drug potent and ready for a long time. To operate the system and to make an intravenous (IV) puncture by a standard needle carrier a professional nurse is required. The system is not adapted for self-administration of thrombolytic therapy.

An IV needle carrier assembly is described in U.S. Pat. No. 4,170,993. It includes a delta-shaped base plate and IV needle carrier-receiving barrel, secured to the base plate. An adhesion tape affixed to the base plate anchors the plate to the skin of the patient. The needle can be moved in two positions, rearward and forward. In the latter position it is placed for puncturing the vein. After establishing an IV access the base is affixed by the adhesion tape for the assembly to retain its place on the skin. This IV needle assembly is intended to be used by a medical professional and is not adapted to gaining an IV access by a patient himself.

SUMMARY OF THE INVENTION

An object of the present invention is to provide an apparatus and method for intravenous infusion of thrombolytic agents and supportive medication as early as 20–30 minutes after the onset of the heart attack symptoms.

Another object of the present invention is to provide an apparatus capable of being in a stand-by position continuously for several years.

Yet another object of the invention is to provide numerous standard schedules of delivery of medications, enabling a cardiologist to select an appropriate care for covering the needs of different patients.

Another object of the present invention is, in case of inability to promptly contact a personal cardiologist or other qualified physician, to provide a cardiac patient with an option to self-diagnose an acute myocardial infarction and self-administer the thrombolytic therapy.

Another object of the present invention is to provide a simple and easy to use needle carrier adapted for gaining IV access by a patient himself or another person without special advanced medical training.

Yet another object of the invention is to provide a low temperature environment for the library of medications ensuring preservation of their potency for several years.

Yet another object of the present invention is to provide a library of medication for thrombolytic therapy and supportive care for the treatment of a heart attack. Provided medication can be in a lyophilized or liquid form.

Another object of present invention is to provide to a personal cardiologist or other qualified physician remote access to the control of the apparatus via the Internet or other information network.

Another object of the present invention is to provide an apparatus for IV infusion, that is highly automated and, after activation, does not require any intervention of an operator.

Still another object is to make the system portable and battery powered, so it can be maintained in a stand by state at a residence, in a car, in an aircraft, or in the field.

The fore mentioned objects are achieved by the present invention, which provides an apparatus and method for emergency treatment of a myocardial infarction. The apparatus comprises a library of medications, a highly automated infusion pump, controlled by a microprocessor, an intravenous needle, providing an access to the patient's circulatory system, a set of valves and conduits, providing fluid communication between the pump, the needle, the medications vials and a bag of solvent used for reconstitution of the lyophilized medications. These medications are placed into a sterile compartment, in which temperature is reduced to 4 C. or lower. This temperature guarantees protein thrombolytic drug stability during 3–5 years if the cooler is not off more than 1–3 months total.

The invention is intended to be used in the out-of-hospital settings like a residence, a car, a passenger aircraft, a hotel, a nursing home and the like.

This invention provides an opportunity to a patient himself to start the thrombolytic therapy right after the onset of cardiac pain, only 20–30 minutes after an occlusion in coronaries had been diagnosed (independently by the patient him/herself or after a consultation with a physician). To activate the system and start the therapy the patient should perform very simple operations with a highly automated infusion system. First, after activation the system reconstitutes the lyophilized drugs and primes itself by venting the air to avoid an air embolism. When the system is ready for infusion, it sends a message to the operator and waits for a command to start infusion. At that time the patient should gain an IV access by puncturing a vein on his/her wrist, thereby fluidly connecting the infusion apparatus with the patient's circulatory system. As soon as the access to the patient's vein is established, the thrombolytic and concomitant therapy can be started at any moment. As the treatment starts the system uses as a default a predetermined infusion schedule, preselected by a personal physician of the patient. The state of the patient during infusion can be evaluated by a physician via a phone line though conversation, or other diagnostic means like ECG with an Internet interface, capable of sending data to the physician. The system can be stopped at any moment and, depending on the state of the patient, the infusion schedule can be changed via the Internet by a qualified physician or by the operator (patient) directly. With the thrombolytic and supportive therapy in progress all efforts should be undertaken to transport the patient to an emergency room in a hospital, where the patient can be treated further by qualified cardiologists. The information about all medications infused into the patient's circulatory system, and the schedules of their infusion are stored in the data acquisition system of the apparatus and are available for the qualified personnel in the emergency room of the hospital.

This invention is intended to be used by well-informed patients experiencing an early stage of a heart attack. Individuals who already had a heart attack, are good candidates for using the apparatus. The term well-informed patients means that these patients not only are familiar with the basics of the cardiovascular disease but also were instructed in details by their personal cardiologist how to use this apparatus, how to communicate with the physician during the onset of a heart attack, what symptoms are important for the correct diagnosis or self-diagnosis of his/her conditions, if by some reasons the contacts with a cardiologist are impossible. In this case the patient must rely upon his/her own judgments and an automated infusion of drugs which will be performed according to the schedules preselected by the patient's physician.

The present invention provides thrombolytic therapy for cardiac patients at the earliest stage of a heart attack, before any necrosis of myocardium or other irreversible changes occur. Right after an occlusion of a coronary artery has happened, the thrombus is weak and is easier to dissolve. It requires less time and amount of thrombolytic agent for restoring patency of the occluded artery and thus results in lower chances of bleeding complications, the major side effect of thrombolytic therapy. In addition, at the early stage of thrombosis, there is no significant difference in efficiency between different thrombolytic drugs (SK or t-PA). So, an early thrombus can be efficiently dissolved by a cheaper streptokinase (SK), cost of which is about 10% of that of t-PA. The overall value of the present invention is provided by the ability of early TT to completely salvage patient's myocardium, resulting in significantly lower morbidity and mortality.

The present invention is designated for use by emergency personal with limited or no medical training in nursing homes, passenger aircrafts and the like, and by well-informed high heart attack risk cardiac patients. The intended individual users should be cautiously screened by a qualified cardiologist before prescribing them an opportunity to buy a system and self-administering the thrombolytic drugs. Before activating the system and starting TT individual users have to diagnose a coronary artery occlusion relying upon their symptoms. The pain of an acute MI typically lasts for at least 30 min, it is unrelenting and does not respond to nitroglycerin. Pain that is not relieved by nitroglycerin or nifedipine challenge (ruling out coronary vasospasm) would indicate occlusive thrombus instead of unstable angina.

The objects, features, and advantages of the present invention are evident for those skilled in the art from the following description of a preferred embodiment of the invention with reference to the accompanying drawings.

DETAILED DESCRIPTION OF THE PREFERRED EMBODIMENT

Figure 1:
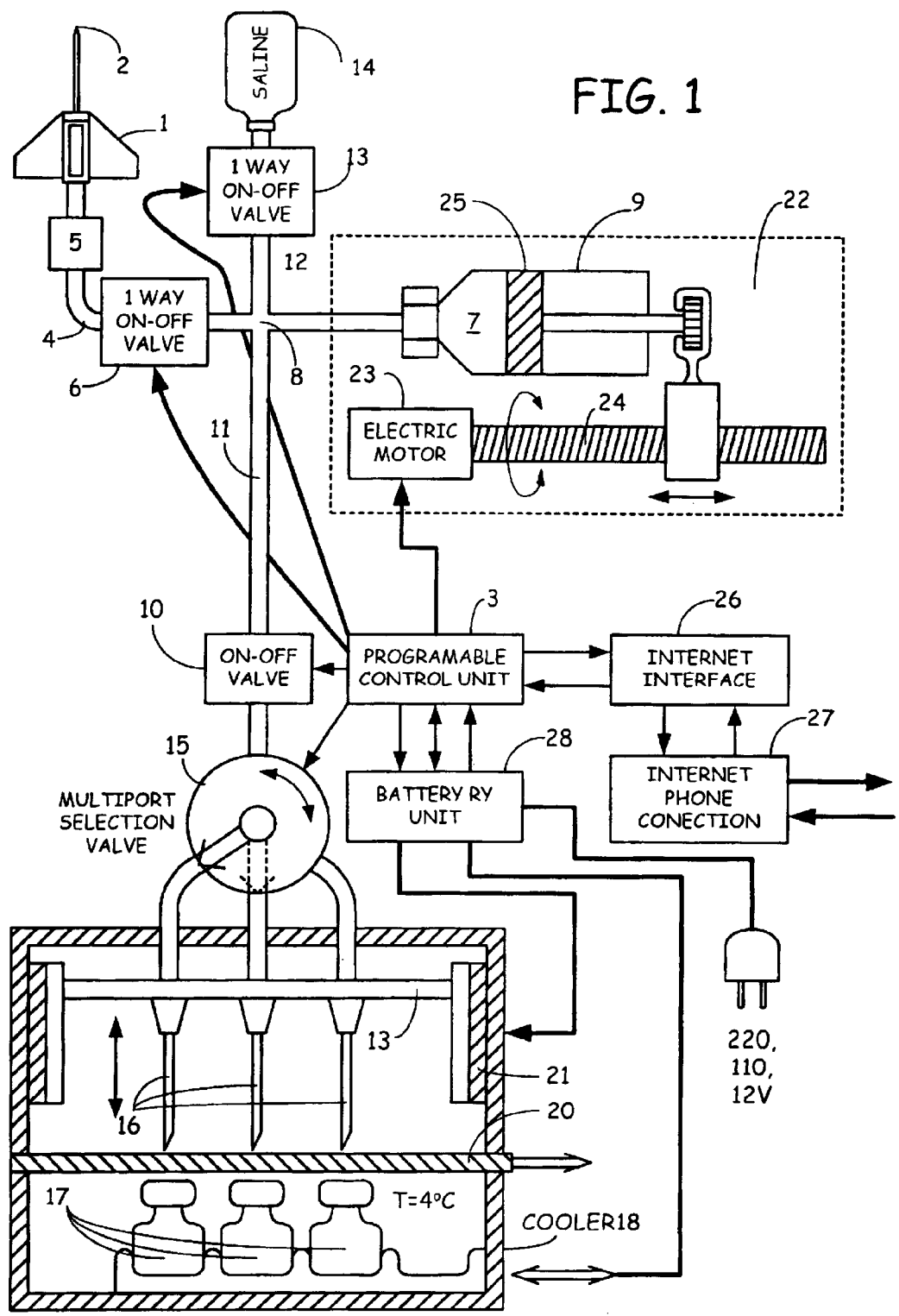
FIG. 1 is an apparatus for out-of-hospital thrombolytic and supportive therapy.

The present invention is schematically shown in the FIG. 1. A needle carrier 1, which includes an IV needle 2, is fluidly connected via a conduit 4 to an outlet 7 of a syringe 9. Hydrophilic filter 5 prevents accidentally trapped air bubbles from entering the patient circulation. One-way valve 6 separates the needle conduit 4 from a conduit star junction 8, connected to the syringe outlet 7. The valve 6 has two positions: "on", which allows the liquid from the syringe outlet 7 to flow to the infusion needle 2 under appropriately applied pressure, and "off", which completely shuts the passage. In the "off" position the valve 6 prevents blood from the patient's vein from entering the conduit 4 and farther into the syringe when vacuum is in the syringe.

Another one-way "on-off" valve 13 controls the passage of fluid from a saline diluent reservoir 14 via a conduit 12 to the conduit star 8. It also has two positions: in "on" position the conduit 12 is open and when vacuum is applied saline can be sucked into the syringe outlet 7. In the "off" position the conduit 12 is shut off, and the fluid communication between the saline reservoir 14 and the syringe is blocked.

Conduit star 8, which fluidly connects the syringe outlet 7, infusion needle 2 and the saline reservoir 14, is also connected to a conduit 11, leading to a multi-port selection valve 15. The multi-port valve 15 is designed to separately communicate the conduit 11 with a needle set 16. The needles are adapted to further communicate with drug vials from a medication library 17. By demand of the control unit 3 the multi-port valve 15 may connect the syringe to a selected drug vial. The drug library 17 is disposed in a hermetic sterile department of a cooler 18, preferably, a thermoelectric cooler. A needle set 16 is secured in an engaging mechanism 19. A thermally insulating wall 20 is removed or punctured through by the needles during activation of the system.

When the system is activated, the engaging mechanism 19 moves the needle set along a rail 21, a part of engaging mechanism 19, forcing all needles to prick all rubber caps of multiple vials simultaneously and thus ensuring fluid communication of the conduit 11 with the drug library 17. The needle set is propelled along the rail 21 by hand or automatically by an electro motor, not shown in FIG. 1. The syringe 9 is the main part of an automated IV pump 22, which also includes an electric motor 23 and a worm mechanism 24, transforming rotational motion of the motor into a translational push-pull motion of the piston 25 in the syringe 9. The programmable control unit 3 of the system controls "on-off" positions of the valves 6, 10, 13, 15, the longitudinal position of the piston 25 in the syringe 9, and the speed of its motion, defining the intravenous infusion rate.

The control unit has several standard programs for priming the system, reconstitution of the drugs, preparing predetermined concentrations of drugs in saline solution, and their delivery in predetermined amounts and rates into the patient circulation. The control unit 17 can be reprogrammed remotely by a physician via the a modem connection such as through a phone line or the Internet. For this purpose an Internet interface 26 with a phone connector 27 is provided. Additionally, with advancing wireless technology, such remote programming could be accomplished through the use of wireless communication devices. A battery with recharging circuitry is provided, which can be powered by any of standard voltages: 110, 220, 12 V.

It will be obvious to those skilled in the art that many modifications may be made within the scope of the present invention without departing from the spirit of thereof, and the invention includes all such modifications.

The present invention having thus been described, other modifications, alterations, or substitutions may now suggest themselves to those skilled in the art, all of which are within the spirit and the scope of the present invention. It is therefore intended that the present invention be limited only by the scope of the attached claims below.

What is claimed is:

1. A method for providing out-of-hospital thrombolytic therapy for substantially preventing the death of a patient's myocardium and early dissolution of a coronary thrombus subsequent to a heart attack, said method comprising:

providing a portable system including:

a library of medication in liquid or lyophilized form including a thrombolytic agent, adjuvant drugs for supportive care during a heart attack and a diluent for reconstitution of drugs;

an intravenous needle providing an access to a patient's circulatory system;

a battery operated infusion pump with a set of conduits, on-off and multi-port valves fluidly communicable with the intravenous needle, a source of a diluent, and vials with drugs in the library;

a battery operated micro cooler adapted for keeping the medication library at reduced temperatures for preservation of their potency over a several year period;

a microprocessor based control unit with a stored set of programs, designed to control operation of the infusion pump and valves to provide priming, drug reconstitution, and preprogrammed intravenous infusion of the thrombolytic agent and supportive drugs;

maintaining the system in stand by state continuously until it is needed;

activating the system within thirty minutes after onset of the symptoms of a heart attack;

gaining an intravenous access to the patient's circulatory system by puncturing a vein with the intravenous needle provided with the system; and starting treatment by infusing the thrombolytic agent and adjuvant drugs within thirty minutes after onset of the symptoms of a heart attack.

* * * * *